United States Patent [19]
Fixel

[11] 4,080,666
[45] Mar. 28, 1978

[54] IMPLANTABLE PROSTHETIC BONE DEVICE

[76] Inventor: Irving E. Fixel, 111 N. 31st Ave., Hollywood, Fla. 33021

[21] Appl. No.: 722,371

[22] Filed: Sep. 13, 1976

[51] Int. Cl.² ............................................. A61F 1/24
[52] U.S. Cl. ................................... 3/1.91; 3/1.911; 3/1.913; 128/92 CA; 128/92 C
[58] Field of Search ..................... 3/1.9–1.913; 128/92 C, 92 CA, 92 R, 92 B, 92 BA, 92 BB, 92 BC

[56] References Cited

U.S. PATENT DOCUMENTS

| 2,685,877 | 10/1954 | Dobelle | 128/92 CA |
| 3,740,769 | 6/1973 | Haboush | 128/92 CA |
| 3,763,855 | 10/1973 | McAtee | 128/92 BC |
| 3,846,846 | 11/1974 | Fischer | 3/1.913 |
| 3,896,505 | 7/1975 | Timmermans | 3/1.913 |

FOREIGN PATENT DOCUMENTS

| 2,558,446 | 7/1976 | Germany | 3/1.912 |

*Primary Examiner*—Ronald L. Frinks
*Attorney, Agent, or Firm*—Richard M. Saccocio

[57] ABSTRACT

An implantable prosthetic bone device which incorporates an improved prestressed anchoring means to provide reinforcement and replacement for fractured or diseased bones and joints.

7 Claims, 1 Drawing Figure

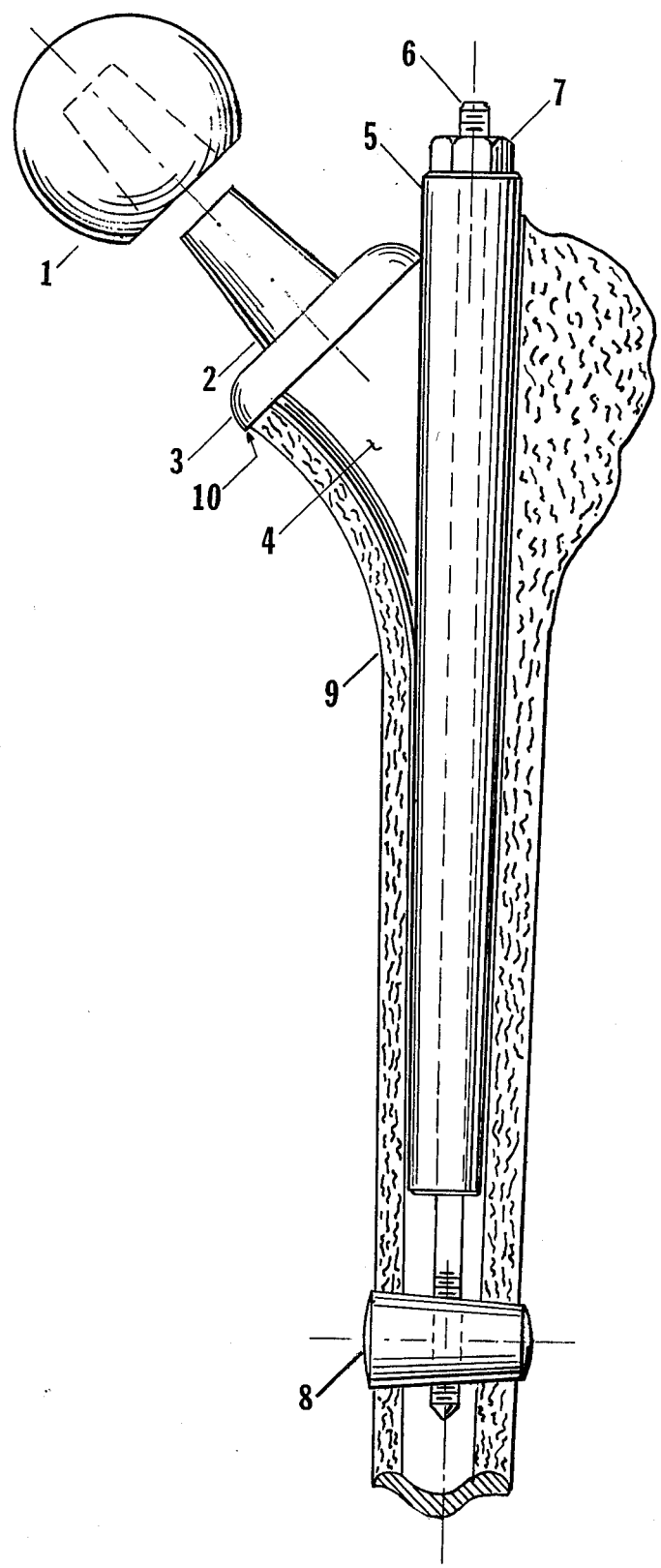

IMPLANTABLE PROSTHETIC BONE DEVICE

BACKGROUND OF THE INVENTION

1. Field of the Invention

The invention generally involves implantable prosthetic devices capable of restoring normal functions to fractured or diseased bones such as the femur, tibia or humerus.

2. Description of Prior Art

Many artificial implanted devices are in use at the present to repair or replace damaged bones. Some of these implants are very simple means such as screws, rods and wires. More complex devices are used to replace certain bones constituting a joint. In many cases the major problem encountered was the difficulty in obtaining a long lasting, strong and secure mechanical connection between the bone and the prosthesis. Biomechanical events causing dislodgement or premature failure of the implants are chiefly the repetitively changing stresses within the prosthesis and the bone. Bonding the implant with cement serves only as a partial solution to this problem. Another important factor is that the live bone will show definite changes in its geometry, hardness and other properties as a function of time. These changes may adversely influence the originally established strength and security of the combined structure of the bond and the prosthesis. Another problem frequently encountered is an oversight in the design by, not recognizing fully the effects of stresses caused by dynamic loads applied to the prosthesis. Also, in many instances there is a dangerously high concentration of stresses confined to a relatively small area. These stresses are responsible for a great number of failures.

BRIEF DESCRIPTION OF THE INVENTION

The purpose of this invention is to provide secure anchoring means for a prosthesis.

It is also the object of this invention to avoid the occurance of undesirable stress concentrations.

Another object of this invention is to prevent failures due to changing dynamic loads.

A further object of this invention is to minimize the possibilities of failure due to material fatigue.

DETAILED DESCRIPTION OF THE PREFERRED EMBODIMENT

The attached drawing, FIG. 1 shows the upper portion of the femur 9 where the femoral head is removed and replaced by artificial means. Said artificial means or prosthesis comprises several component parts.

The intramedullary stem or hollow columnar support member 5 is a long hollow tapered member passing through the centerline of the bone. There is a clerance hole drilled and reamed through the center line of the bone to accept the intramedullary stem 5.

The stem 5 is press fitted into the bone; a brace 4 and a collar 3 are integral parts of the stem 5. The brace 4 is a vertical member, designed to support part of the loads applied to the prosthesis. The collar 3 is provided with a flat surface such that it rests, in bearing relationship, upon the stump of the femoral neck 10 transfering the forces applied to the entire surface of the stump of the femoral neck 10. The tapered attachment pin 2 connects the artificial spherical femoral head 1 to the forementioned assembly.

Another constituent of the prosthesis is the anchor 8, which is a tapered pin press fitted into a matching tapered hole, drilled across the femur 9.

The direction of said hole is at right angles to the centerline of the femur 9. The anchor 8 has also a drilled and threaded hole centrally located and aligned perpendicular to its centerline. The hole is aligned to meet the centerline of the intramedullary stem 5.

A matching thread of a rod 6 is engaged into the threaded hole of the anchor 8. A threaded matching nut 7 engages the upper threaded end of the rod 6 and is tightened to predetermined torque values, whereby the rod 6 will be stretched and put under mechanical stresses. These stresses within the rod 6 will clamp the flat faces of the collar 3 strongly against the exposed surfaces of the stump of the femoral neck 10, requiring equally strong forces of opposite direction to allow any mechanical displacement of the collar 3.

When excessive external forces are applied, there is a tendency to stretch the rod 6 even further, but this will result only in a minute displacement between the parts clamped together, hence will not alter the overall rigidity of the assembly.

Also the stresses within the rod 6 will clamp and force the intramedullary stem 5 into it's previously established press fitted position, and so preventing rotation or movement. The application of cements or any other additional anchoring means to the formentioned prosthesis is optional.

The anchor 8 is inserted into the strongest available area of the femur 9 by choice. Application of the anchor 8 has an obvious effect to the strength of the femur 9. It will noticeably reduce it's tensile strength, but it will change only slightly the weight bearing capability or compressive strength. The resistance against torsional or twisting forces or bending forces will suffer only moderate changes. The reasons for the relatively small changes are evident since this solid anchor 8 is forcefully adjacent to the femur 9 by a press fit, it will therefore support and transfer part of the forces previously carried solely by the femur 9, hence the losses of strength are minimized. The relative large surface areas of the interfaces between the aforementioned prosthesis and the femur 9 maintain a high degree of rigidity to the combined structure of the bone and prosthesis. The basic features of this invention described here are applicable also to replace or repair any other damaged bone or skeletal joint using necessary modifications obvious to those skilled in the art.

What is claimed is:

1. A prosthetic device for repair or replacement of joints of skeletal bones, by implantation in skeletal bone, said prosthetic device comprising
   a hollow columnar support member,
   a brace member rigidly attached to said support member at one end thereof,
   a collar member rigidly attached to an end of said brace member,
   an attachment pin rigidly attached to said collar member and extending outward therefrom,
   a substantially spherical member having means thereon for connecting said spherical member to said attachment pin,
   an anchor member having a first means thereon for engaging a bone to which the prosthetic device is to be implanted and a second means thereon for engaging said support member, and a rod member extending through said support member having a first fastener means thereon for fastening said rod to said anchor member and a second fastener means thereon for fastening the end of said support member remote from said anchor member.

2. The prosthetic device of claim 1 wherein said support member has a tapered outer surface which is adapted to fit within a matching tapered void in a bone to which the prosthetic device is to be implanted.

3. The prosthetic device of claim 1 wherein said collar member includes a substantially flat surface adapted to fit on a suitably prepared substantially flat surface of a bone to which the prosthetic device is to be implanted.

4. The prosthetic device of claim 1 wherein said anchor member comprises a pin and said first means of the anchor member comprises a substantially cylindrical outer surface which is adapted to fit within a suitably prepared hole in a bone to which the prosthesis is to be implanted.

5. The prosthetic device of claim 4 wherein said substantially cylindrical outer surface includes a taper which is adapted to fit forceably within a matching tapered hole in a bone to which the prosthesis is to be implanted.

6. The prosthetic device of claim 1 wherein said anchor member comprises a pin and said first means of the anchor member comprises a tapered outer surface which is adapted to fit forceably within a matching tapered hole in a bone to which the prosthesis is to be implanted and said second means of the anchor member comprises a hole having internal threads said hole having its axis at a substantially right angle to the axis of said pin and wherein said first fastener means of the rod member comprises external screw threads whereby said rod member and said anchor member are in threaded engagement.

7. The prosthetic device of claim 1 wherein said second fastening means of the rod member comprises a nut having internal screw threads, and said rod member is externally threaded and is in threaded engagement with said nut, said nut being in bearing relationship with said end of the support member remote from said anchor member.

* * * * *